US008894833B2

(12) United States Patent
Rasmussen et al.

(10) Patent No.: US 8,894,833 B2
(45) Date of Patent: Nov. 25, 2014

(54) BEVERAGE STERILISATION DEVICE

(75) Inventors: Jan Norager Rasmussen, Olstykke (DK); Steen Vesborg, Gentofte (DK)

(73) Assignee: Carlsberg Breweries A/S, Copenhagen V (DK)

( * ) Notice: Subject to any disclaimer, the term of this patent is extended or adjusted under 35 U.S.C. 154(b) by 1040 days.

(21) Appl. No.: 12/739,705

(22) PCT Filed: Oct. 24, 2008

(86) PCT No.: PCT/DK2008/000373
§ 371 (c)(1),
(2), (4) Date: May 17, 2010

(87) PCT Pub. No.: WO2009/052827
PCT Pub. Date: Apr. 30, 2009

(65) Prior Publication Data
US 2010/0310735 A1   Dec. 9, 2010

(30) Foreign Application Priority Data

Oct. 25, 2007 (EP) .................................... 07388075

(51) Int. Cl.
| | | |
|---|---|---|
| B03C 5/02 | (2006.01) | |
| A61L 2/03 | (2006.01) | |
| A23L 2/48 | (2006.01) | |
| A23L 3/32 | (2006.01) | |

(52) U.S. Cl.
CPC ... *A61L 2/03* (2013.01); *A23L 2/48* (2013.01); *A23L 3/32* (2013.01); *C02F 2201/003* (2013.01)
USPC . 204/547; 422/186; 422/186.03; 422/186.04; 422/22; 426/239; 426/237; 426/241; 99/451; 210/748.01

(58) Field of Classification Search
CPC ............. A23L 2/48; A23L 3/32; A23L 3/005; A23L 3/26; A61L 2/03; C02F 2201/003
USPC .......... 422/186, 186.03, 186.04, 22; 204/547; 99/451; 426/237, 239, 241; 210/748.01
See application file for complete search history.

(56) References Cited

U.S. PATENT DOCUMENTS

| | | |
|---|---|---|
| 4,457,221 A | 7/1984 | Geren |
| 6,030,538 A | 2/2000 | Held |

(Continued)

FOREIGN PATENT DOCUMENTS

| | | |
|---|---|---|
| EP | 1400493 | 3/2004 |
| WO | WO99/63843 | 12/1999 |

(Continued)

OTHER PUBLICATIONS

International Search Report on related PCT application (PCT/DK2008/000373); International Searching Authority (EPO) dated Feb. 10, 2009.

*Primary Examiner* — Xiuyu Tai
(74) *Attorney, Agent, or Firm* — Klein, O'Neill & Singh, LLP

(57) ABSTRACT

A beverage sterilisation device comprises a housing defining an inner space, and having a first and a second end. An electrically insulated fluid path-defining conduit extends through the inner space from the first end to the second end. A first electrode has a first part positioned adjacent to the fluid path and a second part extending perpendicular to the first part. A first counter electrode defines together with the first electrode a first capacitor, and a second electrode having a third part and a fourth part. The third part is positioned adjacent to the fluid path, and the fourth part extends substantially perpendicular to the third part. A second counter electrode defines together with the second electrode a second capacitor. The first counter electrode and the second counter electrode are short-circuited by an electrical connection, and a conductive device is electrically connected between the first electrode and the second electrode. A first trigger point is defined at the second part and remote from the first part, and a second trigger point is defined at the first counter electrode opposite to the first trigger point. The device further comprises an electrical activation circuit for short-circuiting the pair of trigger points and for causing an electric field to propagate from the first trigger point and along the fluid path.

8 Claims, 12 Drawing Sheets

(56) References Cited

U.S. PATENT DOCUMENTS

| | | |
|---|---|---|
| 6,093,432 A | 7/2000 | Mittal et al. |
| 6,150,663 A | 11/2000 | Rosenthal |
| 7,931,811 B2 * | 4/2011 | Ruan et al. ............... 210/748.01 |
| 2004/0084381 A1 | 5/2004 | Korenev |

FOREIGN PATENT DOCUMENTS

| | | |
|---|---|---|
| WO | WO 2004/037301 | 5/2004 |
| WO | WO2005/107821 | 11/2005 |

* cited by examiner

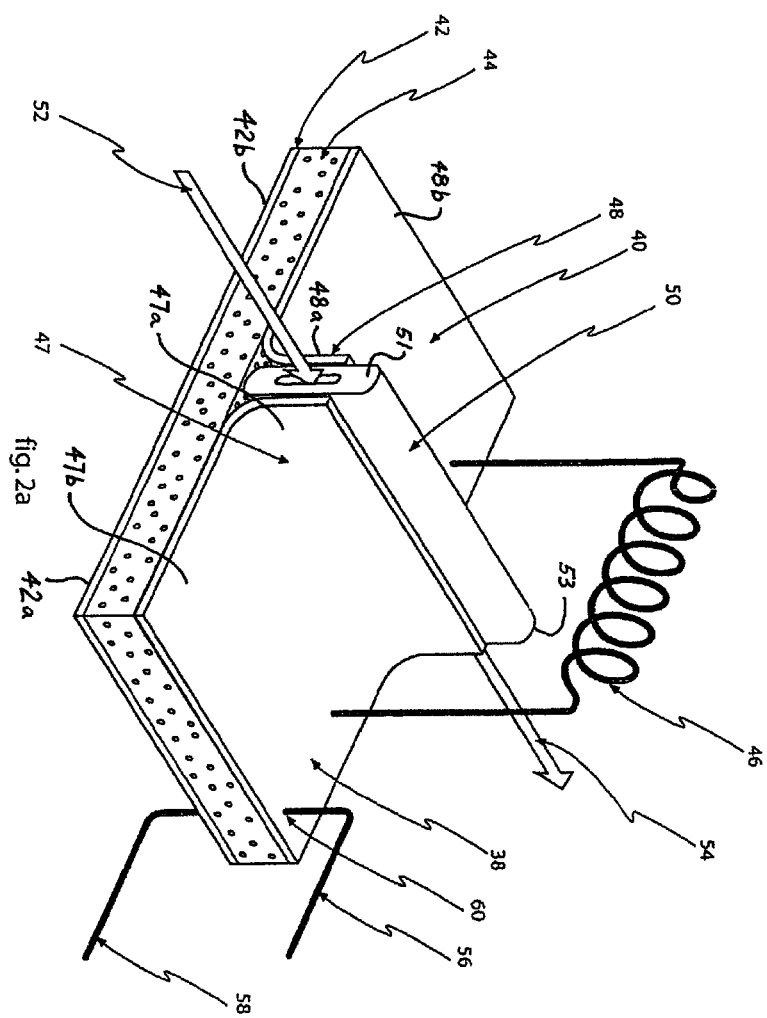

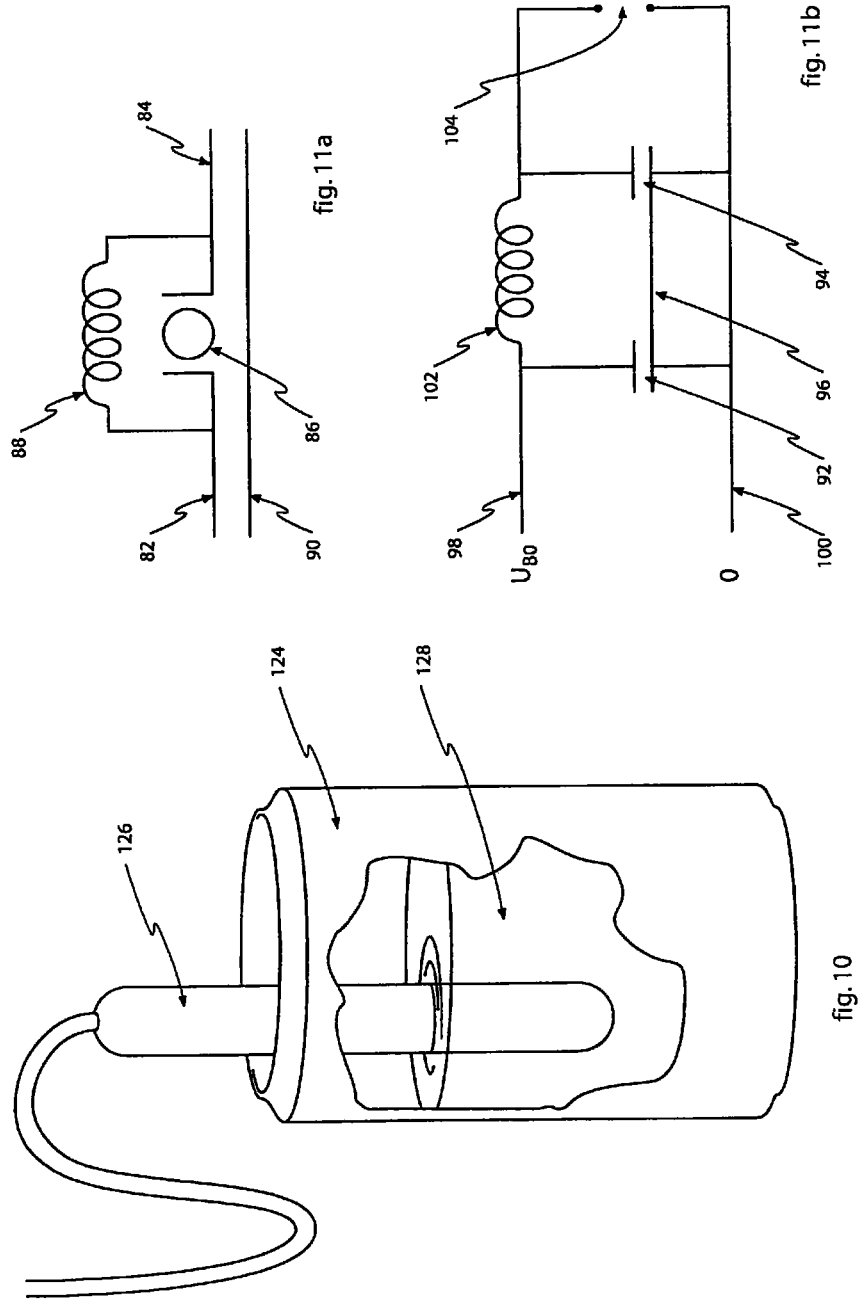

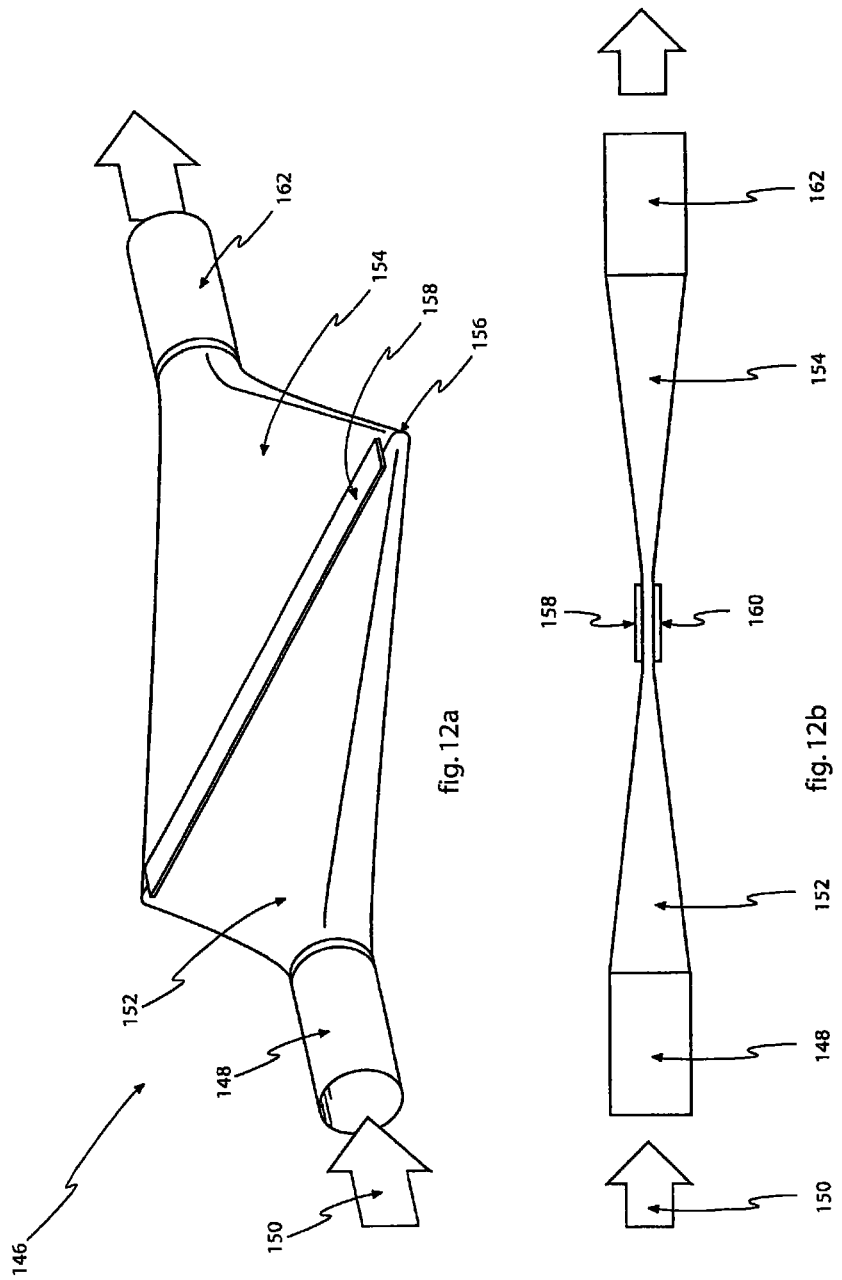

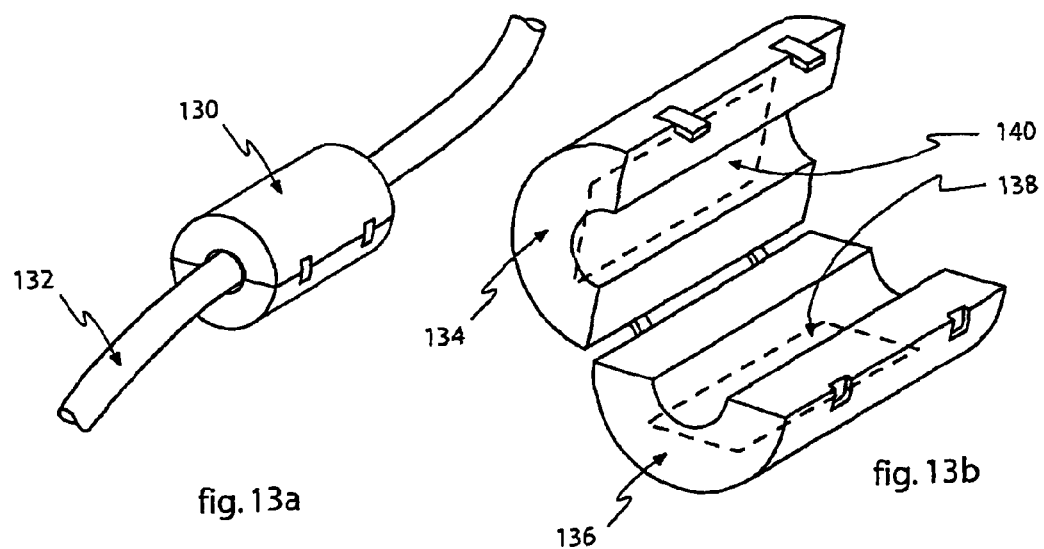
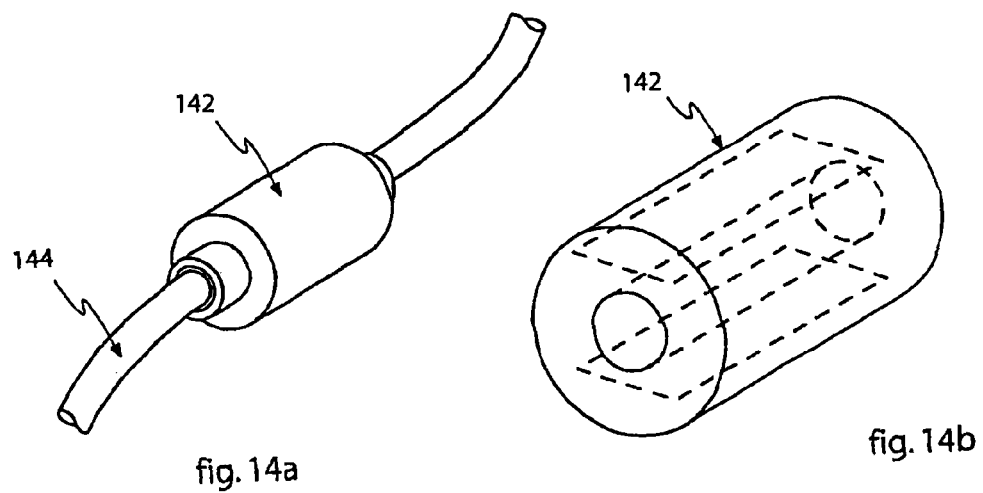

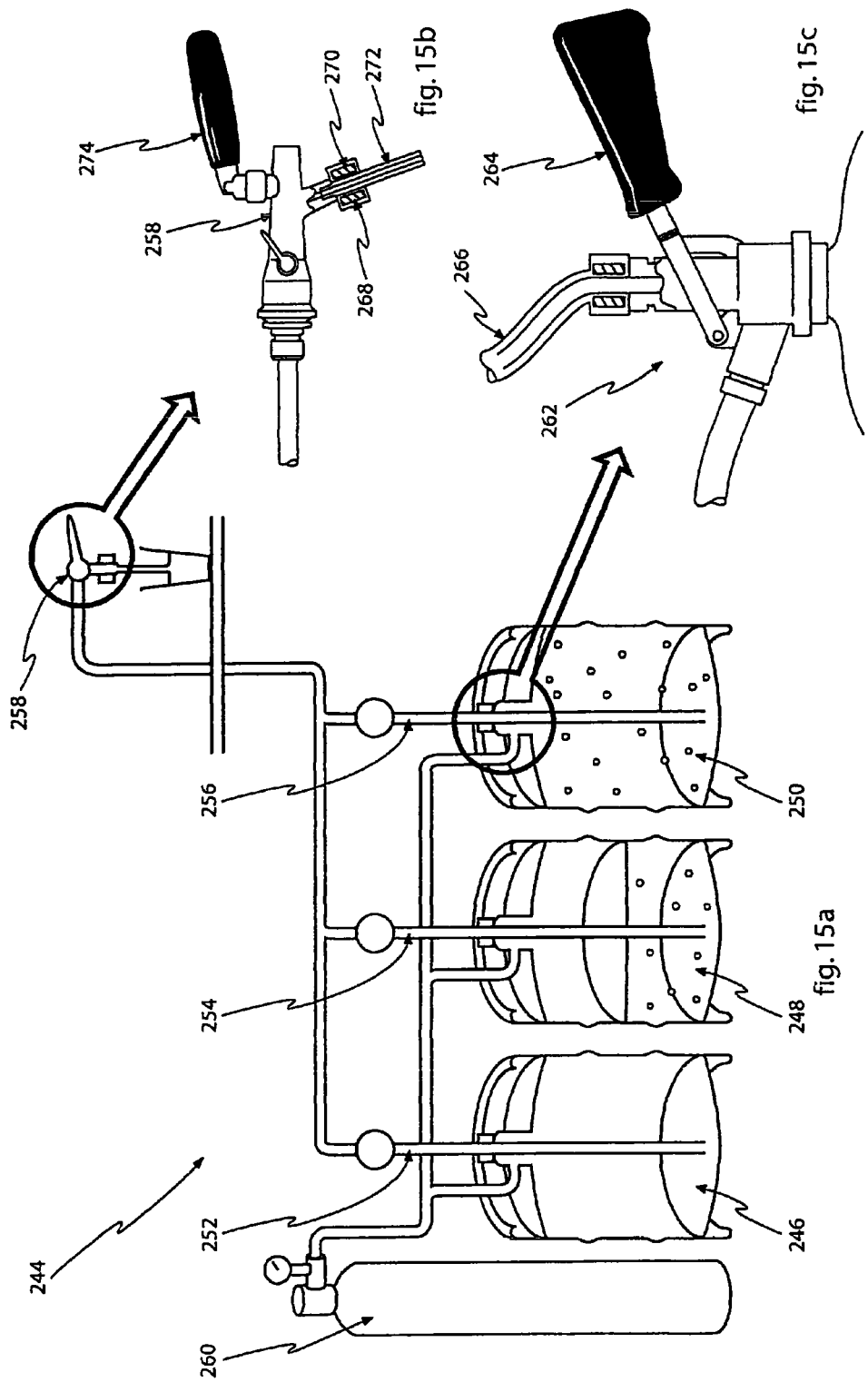

BEVERAGE STERILISATION DEVICE

CROSS-REFERENCE TO RELATED APPLICATION

This application is a national phase filing, under 35 U.S.C. §371(c), of International Application No. PCT/DK2008/000373, filed on Oct. 24, 2008, the entire contents of which are hereby incorporated by reference.

FEDERALLY SPONSORED RESEARCH OR DEVELOPMENT

Not Applicable

BACKGROUND

The present invention relates to methods and apparatuses for sterilising beverages. Any beverage may comprise bacteria. Traditionally, during the process of sterilising beverages, i.e., substantially removing, killing or destroying micro organisms, the beverages have been pasteurised, i.e., heated to a temperature above which micro organisms, in particular bacteria, and not excluding yeast, fungi, virus and/or prions are killed. In some, or most instances this may ruin taste components. Thus there is a need to provide a system and a method for sterilising beverages without altering, changing or in any other way substantially changing the beverage.

One way to kill micro organisms, such as bacteria, is electro-poration, or electro-permeabilisation, which is achieved by causing a significant increase in the electrical conductivity and permeability of the cell membrane by an externally applied electric field. This is also utilised in molecular biology, albeit without killing the cells. Pores are formed when the voltage across a cell membrane exceeds its dielectric strength. If the strength of the applied electric field and/or duration of exposure to it are properly chosen, the pores formed by the electrical pulse reseal after a short period of time, during which extra cellular compounds have a chance to enter into the cell. However, excessive exposure of live cells to electric fields can cause apoptosis and/or necroses, i.e. result in cell death, which is desirable when sterilising beverage.

The present invention provides systems and methods for performing sterilisation of beverage based on such a principle. The systems and methods include subjecting beverage to electric fields, preferably without having any direct contact between the electric field generator and the beverage.

Generally micro organisms in the beverage are also subjected to this electric field. Bacteria have a lipid bilayer membrane. The lipid bilayer membrane is a membrane or zone of a membrane composed of lipid molecules, usually phospholipids. Lipids are amphiphilic molecules since they have polar head groups and non-polar fatty acid tails. The bilayer is composed of two layers of lipids arranged so that their hydrocarbon tails face one another to form an oily core held together by Van der Waals interactions, while their charged heads face the aqueous solutions on either side of the membrane.

SUMMARY

A first aspect of the present invention relates to a beverage sterilisation device, which may comprise:
a housing defining an inner space, the housing having a first and a second end,
an electrically insulated fluid path defining conduit extending through the inner space from the first end to the second end,
a first electrical conductive electrode having a first part and a second part, the first part being positioned adjacent to the fluid path at the conduit, the second part extending substantially perpendicular to the first part,
a first electrical conductive counter electrode defining together with the first electrical conductive electrode a first capacitor of a first specific capacitance,
a second electrical conductive electrode having a third part and a fourth part, the third part being positioned adjacent to the fluid path at the conduit, the fourth part extending substantially perpendicular to the third part and away from the second part of the first electrical conductive electrode,
a second electrical conductive counter electrode defining together with the second electrical conductive electrode a second capacitor of a second specific capacitance,
the first electrical conductive counter electrode and the second electrical conductive counter electrode being short-circuited by an electrical connection,
a conductive device electrically connected between the first electrical conductive electrode and the second electrical conductive electrode,
a pair of trigger points, a first trigger point being defined at the second part of the first electrical conductive electrode and remote from the first part thereof and a second trigger point being defined at the first electrical conductive electrode opposite to the first trigger point,
an electrical activation circuit for short-circuiting the pair of trigger points and for causing an electric field to propagate from the first trigger point and along the fluid path.

The device according to the first aspect of the present invention is contemplated to be used in a variety of settings, including in beverage production facilities, beverage dispensing equipment, and beverage dispensing settings.

The electrodes are used to transmit or emit an electrical signal or field through the insulated beverage or fluid path. As described above, it is contemplated that the presence of an electric field will cause the membrane of bacteria to open and thereby kill or destroy the bacteria. As will be discussed elsewhere the electric field may be static, varying, pulsated, alternating or any combination thereof. The actual electric field strength may be chosen depending on the implementation and setting.

The device according to the first aspect of the present invention may include a power source in the housing. Alternatively, a power source may be connected to the device. This also applies to the other embodiments and aspects of the present invention. The housing is preferably made from plastic material, such as PP, ABS or the like.

In one embodiment, the capacitance of the first capacitor and the second capacitor may be equal. An example could be a capacitance of 5 pF. An embodiment with a capacitance of 5 pF and a voltage of 10 kV would require a power in the order of 0.3 mW, which is a relative low electrical power. It is thus not required to use a large, high power electrical power supply, but allows the use of a small battery while retaining a relatively long service life.

In the device according to the first aspect of the present invention, the housing may be composed of two parts hinged together at one side, the fluid path defined by a depression in each of the parts so that when the two parts are assembled the fluid path is established, the depressions forming a tube receiving structure. This is contemplated to allow the device according to the first aspect to be secured around a beverage dispensing tube, tubing or guide. The tube, tubing or guide should be made from a material allowing electric fields to pass, such material include polymer material, glass and other.

In an alternative embodiment, the housing may include a first connector at the first end constituting a fluid inlet for establishing fluid communication with a first tube, and the housing includes a second connector at the second end constituting a fluid outlet for establishing fluid communication with a second tube. This is contemplated to allow the device to be inserted in a beverage dispensing line composed of two or more tubes or tubing. In such an embodiment, beverage flows through the inside of the housing and not, as above, in a separate tube.

A second aspect of the present invention relates to a beverage sterilisation device that may comprise:
- a housing defining an outer surface and an inner space, the housing having a first and a second end,
- an electrically insulated fluid path defining conduit form by the surface and adapted to receive a tube, the conduit having an open part for receiving and fixating the tube,
- a first electrical conductive electrode having a first part and a second part, the first part being positioned adjacent to the fluid path at the conduit, the second part extending substantially perpendicular to the first part,
- a first electrical conductive counter electrode defining together with the first electrical conductive electrode a first capacitor of a first specific capacitance,
- a second electrical conductive electrode having a third part and a fourth part, the third part being positioned adjacent to the fluid path at the conduit, the fourth part extending substantially perpendicular to the third part and away from the second part of the first electrical conductive electrode,
- a second electrical conductive counter electrode defining together with the second electrical conductive electrode a second capacitor of a second specific capacitance,
- the first electrical conductive counter electrode and the second electrical conductive counter electrode being short-circuited by an electrical connection,
- a constant current maintaining inductor electrically connected between the first electrical conductive electrode and the second electrical conductive electrode,
- a pair of trigger points, a first trigger point being defined at the second part of the first electrical conductive electrode and remote from the first part thereof and a second trigger point being defined at the first electrical conductive electrode opposite to the first trigger point,
- an electrical activation circuit for short-circuiting the pair of trigger points and for causing an electric field to propagate from the first trigger point and along the fluid path.

The device according to the second aspect of the present invention is adapted to receive a tube or tubing for transporting a beverage in a recess or opening formed on the outside of the housing. The recess may include protruding areas for retaining the tube or tubing in the recess. Alternatively, or in combination therewith, further retaining means, e.g. straps, wires or the like may be used.

The electrical components of the device according to the second aspect are similar to those mentioned in relation to the device according to the first aspect of the present invention.

In a particular embodiment the trigger points may constitute Blumlein discharge propagation points and the electrical activation circuit may be a Blumlein short-circuiting circuit for short-circuiting the Blumlein propagation points. Alternatively the electrical activation circuit may be constituted by a spark gap, a spark coil, a spark plug, a thyratron, any other suitable electrical element or any combination of the mentioned elements. Also devices for magnetic pulse compression may be included in the system. Such a device may be used for generating the pulse or current just prior to activating the circuit and generating the electric field.

The activation circuit is used to start an electric field or wave that eventually travels through the beverage and interacts with the membrane of micro organisms, such as bacteria, as described above.

In an advantageous embodiment, the first electrical conductive counter electrode may be positioned opposite the second part of the first electrical conductive electrode and extending so that a substantially constant distance is maintained between the second part of the first electrical conductive electrode and the first electrical conductive counter electrode. This is contemplated to ensure that the capacitor defined by the electrodes functions correctly and without any defects or unwanted or uncontrolled electric field being generated. Similarly, the second electrical conductive counter electrode may be positioned opposite the second part of the second electrical conductive electrode and extending so that a substantially constant distance is maintained between the second part of the second electrical conductive electrode and the second electrical conductive counter electrode.

In a further advantageous embodiment, the first electrical conductive counter electrode and the second electrical conductive counter electrode may be formed as a single electrode. This may simplify the implementation of the construction. Alternatively, the first electrical conductive counter electrode and the second electrical conductive counter electrode may be formed as discrete electrodes and a direct electrical connection is formed between the first electrical conductive counter electrode and the second electrical conductive counter electrode. This is contemplated to achieve the same effect as the single electrode embodiment above.

In a special embodiment, a short-circuit point may be defined on the second part of the first electrical conductive electrode remote from the first part of the first electrical conductive electrode.

In a further particular embodiment, the first electrical conductive counter electrode may be constituted by a first coaxial cable electrically connected to the first electrical conductive electrode. Still further, the second electrical conductive counter electrode may be constituted by a second coaxial cable electrically connected to the second electrical conductive electrode. Even still further, both the first and the second electrical conductive counter electrode may be constituted by coaxial cables. This is contemplated to provide an alternative embodiment of the capacitors. In a specific embodiment, a shielding part of the first coaxial cable may be electrically connected to a shielding part of second coaxial cable.

As described above the fluid or beverage may flow through the housing. In that case, the fluid path may be constituted by a tubular conduit within the housing. The conduit is then contemplated to ensure that the beverage does not enter the inside of the housing. The cross-section of the conduit preferably has a geometry similar to that of the tube or tubing connected to the device according to the present invention. Usually this geometry is substantially circular.

Advantageously, the conduit may be made from glass, plastic, Teflon® brand polytetrafluoroethylene (PTFE) or any other suitable material. The material should preferably be electrically insulating or non-conductive. Alternatively, the material may be electrically conductive.

The housing may be made from a plastic material. The material used for the housing is non-conductive and does not affect the electric field generated.

An inner space may be defined by the housing and a gas may be included in the inner space in the housing and at least partly surrounding the fluid path. The inner space may alternatively be evacuated, i.e. substantially without gas.

A thyratron may be positioned within the housing in electrical connection with the first electrical conductive electrode. The thyratron may be used for initiating the electric field. The thyratron may be electrically connected to the short-circuiting point.

As described above, an electrical power source may be positioned in the housing. Further, the electrical power source may be a battery, such as a Lithium Ion battery. Any other suitable battery type may be used.

Preferably, the first capacitor has a capacitance in the interval 1 pF to 50 pF. Further, the constant current maintaining inductor may be a coil. The coil may have an inductance in the order of 1 pH to 1 mH.

The beverage sterilisation device according to the first and/or second aspects may be included in a beverage dispensing apparatus or connected to a beverage dispensing line included in a beverage dispensing line. This includes draught beer dispensing apparatuses and systems as well as water dispensing apparatuses.

The electrical conductive device mentioned above may include or may be constituted by an inductor, a resistor, a capacitor or any combination thereof. The choice of component may depend on desired use or power consumption.

A third aspect of the present invention relates to a method of sterilising a beverage conducted through an electrically insulated fluid path, the method may comprise the steps of:

providing a sterilisation device including a housing defining an inner space, the housing having a first and a second end, the electrically insulated fluid path defined by a conduit extending through the inner space from the first end to the second end, a first electrical conductive electrode having a first part and a second part, the first part being positioned adjacent to the fluid path at the conduit, the second part extending substantially perpendicular to the first part, a first electrical conductive counter electrode defining together with the first electrical conductive electrode a first capacitor of a first specific capacitance, a second electrical conductive electrode having a third part and a fourth part, the third part being positioned adjacent to the fluid path at the conduit, the fourth part extending substantially perpendicular to the third part and away from the second part of the first electrical conductive electrode, a second electrical conductive counter electrode defining together with the second electrical conductive electrode a second capacitor of a second specific capacitance, the first electrical conductive counter electrode and the second electrical conductive counter electrode being short-circuited by an electrical connection, a conductive device electrically connected between the first electrical conductive electrode and the second electrical conductive electrode, a pair of trigger points, a first trigger point being defined at the second part of the first electrical conductive electrode and remote from the first part thereof and a second trigger point being defined at the first electrical conductive electrode opposite to the first trigger point, an electrical activation circuit for short-circuiting the pair of trigger points and for causing an electric field to propagate from the first trigger point and along the fluid path;

providing the beverage in the electrically insulated fluid path, charging the first and the second electrical conductive electrodes, activating the short-circuiting point so as to generate an electric field through the electrically insulated fluid path; and repeating the charging and the activating.

A fourth aspect of the present invention relates to a method of sterilising a beverage conducted in an electrically insulated fluid path, the method comprising:

a housing defining an outer surface and an inner space, the housing having a first and a second end, the electrically insulated fluid path defining conduit form by the surface and adapted to receive a tube, the conduit having an open part for receiving and fixating the tube, a first electrical conductive electrode having a first part and a second part, the first part being positioned adjacent to the fluid path at the conduit, the second part extending substantially perpendicular to the first part, a first electrical conductive counter electrode defining together with the first electrical conductive electrode a first capacitor of a first specific capacitance, a second electrical conductive electrode having a third part and a fourth part, the third part being positioned adjacent to the fluid path at the conduit, the fourth part extending substantially perpendicular to the third part and away from the second part of the first electrical conductive electrode, a second electrical conductive counter electrode defining together with the second electrical conductive electrode a second capacitor of a second specific capacitance, the first electrical conductive counter electrode and the second electrical conductive counter electrode being short-circuited by an electrical connection, a constant current maintaining inductor electrically connected between the first electrical conductive electrode and the second electrical conductive electrode, a pair of trigger points, a first trigger point being defined at the second part of the first electrical conductive electrode and remote from the first part thereof and a second trigger point being defined at the first electrical conductive electrode opposite to the first trigger point, an electrical activation circuit for short-circuiting the pair of trigger points and for causing an electric field to propagate from the first trigger point and along the fluid path;

providing the beverage in the electrically insulated fluid path, charging the first and the second electrical conductive electrodes, activating the activation circuit so as to generate an electric field through the electrical insulated fluid path; and repeating the charging and the activating.

The method according to the third and/or fourth aspect may be performed using an apparatus according to the first and/or second aspect of the present invention.

In one embodiment of the present invention, a flow meter may be present. The flow meter is contemplated to be used for detecting when beverage flows in a fluid guiding channel, such as the tube or tubing discussed above. This may allow the device to perform the sterilisation at two different rates, one fast rate when the beverage is being dispensed or at least flows in the tube or tubing, and one slower rate when the beverage does not flow or is not being dispensed. One example could be a draught beer dispensing apparatus where the flow meter is included at the coupling between the beer container and the beer line, i.e. a tube or tubing. When beer is dispensed, e.g. from a tap, the flow meter will detect a change in flow speed, and may activate the sterilisation device or at least cause it to be shifted into a different mode where an electric field is applied at a high repetition rate. When no beverage is being dispensed, the sterilisation device may emit the electric field less often.

In a bar setting with one or more beverage storage containers being connected to a beverage guiding line to a beverage dispensing tap, it is contemplated to be an advantage to mount a sterilisation device according to the present invention at the place where the one or more beverage containers are connected to the beverage guiding tube or line and one more at the beverage dispensing tap. When a beverage container is empty, a new, filled one is connected to the beverage dispensing line or tube. When this coupling is performed it is possible that contaminants are introduced into the system. Also, the dispensing tap is exposed to the bar surroundings and thereby also to contaminants. At these places it may therefore be advantageous to place or mount a beverage sterilisation device according to the present invention. Further, the addition of a flow meter is contemplated to enhance the advantage, as the flow meter is further contemplated to reduce to energy consumption of the device over time.

When no beverage is being dispensed from a tap, there may be a small residue of beverage in the tip of the tap, and as the tip is open-ended and exposed to surrounding environment, there is a risk that bacteria and other micro organisms enter the tip and thereby pollute the beverage. Therefore, it is contemplated to be advantageous to position or mount a beverage sterilisation device at the tip of a tapping device. Additionally, a flow meter for detecting when beverage is being dispensed may be included. When no beverage is being dispensed, any micro organisms present in the tip travel only relatively slowly, e.g. in a direction from the opening of the tip and upstream of the tip. Therefore, it may be sufficient to perform sterilisation of the beverage present in the tip fewer times per time unit than when beverage is being dispensed. The detection of beverage flowing or not may also be linked to a handle or operation part of the tap.

The charging and short-circuiting or activation may be repeated with a frequency of 0.01 Hz to 1 kHz for a first period of time. Alternatively, the charging and short-circuiting or activation may be repeated non-periodically. The charging and the short-circuiting may be repeated non-periodically for a second period of time. The second period of time may be 10 seconds or may be controlled by a flow meter or other flow detection means as discussed above.

In the method according to the third and/or fourth aspect of the present invention the system used may include any of the features according to the system or apparatus according to the first and/or second aspect.

A fifth aspect of the present invention relates to a beverage guiding and sterilising system that may comprise:
  a beverage inlet section for receiving beverage, the beverage inlet section defining a first cross-sectional geometry allowing a laminar flow of the beverage or substantially laminar at a first maximum flow speed, the first cross-sectional geometry defining a first cross-sectional area, a first maximum width and a first minimum width defined by the first cross-sectional geometry, a first ratio of the first maximum width to the first minimum width being within the interval 1 to 10,
  a first transitional section having a first and an opposite second end, a cross-sectional geometry identical to the first cross-sectional geometry being defined at the first end,
  a beverage sterilisation section having a second cross-sectional geometry, the beverage sterilisation section including a set of electrodes for generating an electric field, the electric field passing through the beverage in the beverage sterilisation section,
  the first transitional section defining at the second end a cross-section geometry identical to the second cross-sectional geometry, the first transitional section defining a first transitional section length from the first end to the second end, the cross-section of the first transitional section changing along the first transitional section length from the first cross-sectional geometry to the second cross-sectional geometry so that when the beverage flows through the first transitional section the beverage flows with a substantially laminar flow, the second cross-sectional geometry defining a second cross-sectional area, a second maximum width and a second minimum width defined by the second cross-sectional geometry, a second ratio of the second maximum width to the second minimum width being within the interval 10 to 10.000, and
  the beverage sterilisation section being in fluid communication with the first transitional section at the second end thereof.

An additional embodiment may have an electrode and a tube, tubing or pipe in a coaxial or concentric configuration, where the electrode is positioned either inside the inner part of the tube, tubing or pipe, or at the inner wall of the tube, tubing or pipe. The shape or geometry of the cross-section of the pipe, tube or tubing is preferably circular, but may also be elliptical, square, polygonal or any combination thereof.

The electric field may propagate perpendicular to the direction of the beverage flow, parallel to the beverage flow or at a specific angle relative to the beverage flow direction. Preferably the beverage flow includes a part where the beverage flows in a substantially straight line, and the direction of the electric field may be defined relative to this part of the beverage flow.

The electrodes may also be arranged in a Blumlein configuration where the electric field propagates fast along the flow direction of the beverage. The above remarks regarding the electrode configurations apply to all aspects of the present invention.

The system according to the fifth aspect is contemplated to be used in beverage production facilities where it is important that the beverage flows with a laminar or substantially laminar flow. This may be the case when brewing beer, where it is undesirable to have brewed beer flow turbulently so that foam is formed in the production system. However, a small or insignificant amount of turbulent flow may be acceptable. This is similar for the production of carbonated soft drinks.

The laminar flow should be maintained in order to prevent gasses to be released from the beverage however; a small amount of non-laminar flow may be acceptable. The transition section should be formed without any abrupt transitions. The transformation from the first cross-section geometry to the second cross-section geometry should be smooth.

The set of electrodes may generate a static electric field, a pulsating electric field, a varying electric field, an alternating electric field, an AC-field, a DC-field, a RE-field, a HF-field, a DC-field with an AC-overlay or any combination thereof. The type of field may depend on several considerations, such as surroundings, EMC requirements or compliance, speed or velocity of beverage, and the size or width of the beverage sterilisation section to be exposed to the electric field.

In one embodiment the electric field may be generated using a high voltage of 50 kV. The maximum width of the beverage sterilisation section may be in the order of 1 to 5 meters and the minimum width may be 1 to 5 mm. The flow speeds are usually less than 10 m/s.

As the beverage flows in the system and the electrodes are kept stationary, there is still a relative movement between the beverage and the electrodes.

In one embodiment the beverage sterilisation section may be formed by part of the first transitional section and/or the second transitional section. The electrodes may then be positioned on top of one or both transition section or sections. Further, the first and second transition sections may be integrally formed.

The beverage sterilisation section may be a separate part interconnecting the first transitional section and the second transitional section. Further, the first and second transition sections may be integrally formed with the beverage sterilisation area or section.

Specifically the first transitional section and/or the second transitional section may be made from a non-electrical conductive material. This is contemplated to ensure that the electric field is able to pass through the system and the beverage. Further the beverage sterilisation section may be made from a non-electrical conductive material.

It is advantageous that the first cross-sectional geometry may be substantially circular, elliptical, polygonal with an overall round geometry, or any combination thereof. The first cross-sectional geometry may correspond to the geometry of a tube or pipe in a production facility, such as in a brewery.

As above, an additional embodiment may have an electrode and a tube, tubing or pipe in a coaxial configuration, where the electrode is positioned either inside the inner part of the tube, tubing or pipe, or at the inner wall of the tube, tubing or pipe.

The second cross-sectional geometry may be substantially rectangular, square or elliptical or a combination thereof. The second cross-sectional geometry should be formed so that the electric field should travel a minimum distance. Large distances require higher voltages and thus higher power consumption and possible problems with interference with other equipment etc.

The system according to the fifth aspect of the present invention may include features mentioned in relation to the first, second, third and/or fourth aspect of the present invention.

BRIEF DESCRIPTION OF THE DRAWINGS

The present invention will now be discussed in more detail with reference to the figures, in which.

FIGS. 2a and 2b are schematic illustrations of capacitor systems, FIG. 10 is a schematic illustration of beverage in a can being sterilised, FIGS. 11a and 11b are schematic illustrations of circuits for sterilising beverages, FIGS. 12a and 12b are schematic views of a system for sterilising beverage in a production facility, FIGS. 13a and 13b are schematic views of one embodiment of an apparatus for sterilising beverage flowing in a tube, FIGS. 14a and 14b are schematic views of another embodiment of an apparatus for sterilising beverage flowing in a tube, FIG. 15a is a schematic illustration of a system comprising three beverage containers and a beverage dispensing tap, FIG. 15b is a schematic zoomed view of a beverage dispensing tap, FIG. 15c is a schematic zoomed view of a connector for a beverage container.

DETAILED DESCRIPTION

Figure 1:
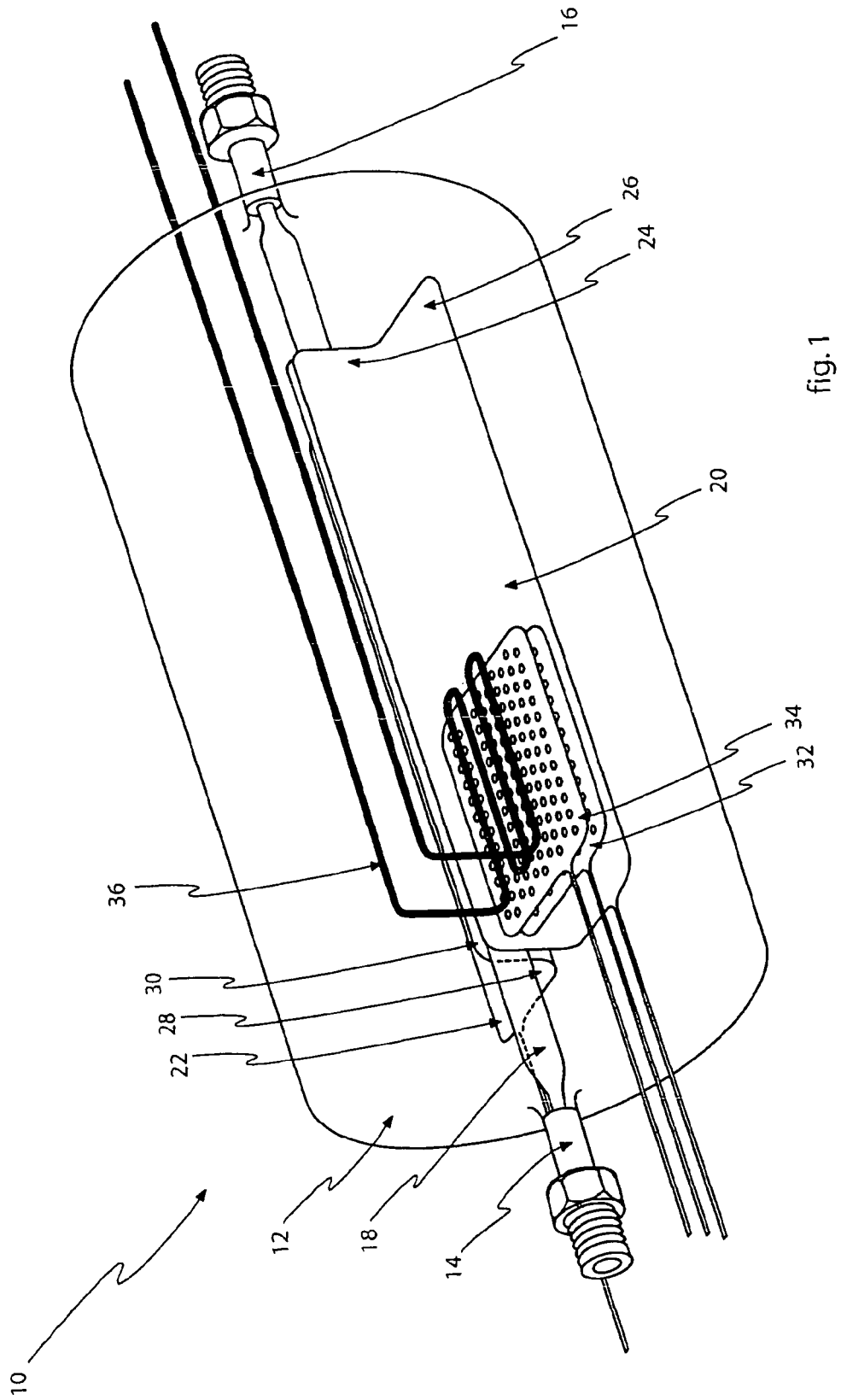
FIG. 1 is a schematic illustration of a first embodiment of a sterilisation system.

FIG. 1 is a schematic view of a system 10 for sterilising beverage. In the presently preferred embodiment the beverage is beer but other beverages may be used such as water, fruit juice, soft drink or wine. The system 10 comprises a housing 12 with adaptors 14 and 16 for connecting to a beverage fluid path, e.g. in a brewery or in a beverage dispensing setup, such as in a bar or the like.

The housing 12 includes a fluid guiding tube 18 in fluid communication with the adaptors 14 and 16 for establishing a fluid path through the housing 12.

In the embodiment shown in FIG. 1 the housing 12 is made from glass material. The tube 18 is also made from glass and may be formed integrally with the housing 12. The housing 12 is hollow and evacuated to form a vacuum inside the housing 12. In alternative embodiments the housing may be filled with a gas, e.g., an inert gas or metal vapour.

The housing 12 further comprises two metallic plates 20 and 22. The two plates 20 and 22 are positioned along the length of the fluid guiding tube 18. As the tube 18 is substantially straight, the plates 20 and 22 are positioned parallel to the tube 18.

The plates 20 and 22 each comprise two parts, 24, 26 and 28, 30, respectively. Illustrated by the plate 20, the two parts 24 and 26 are positioned substantially perpendicular to each other. The construction will be described in more detail with reference to the other drawings. The plates 20 and 22 are made from an electrically conductive metallic material. The plates 20 and 22 form part of a capacitor system.

The system 10 further comprises two grids 32 and 34. The grids are part of a thyratron used to start an electromagnetic wave travelling in the plate 20, through the tube 18 to the plate 22. The grids 32 and 34 provide a trigger effect. The normal grid potential is negative with respect to the cathode and prevents electrons from flowing to the plate. Other suitable ignition devices may be used. Also, devices for magnetic pulse compression may be included in the system. This may be used for allowing the signal to be generated at the last moment before short-circuiting the system and activating the Blumlein circuit.

A thyratron is a type of gas filled tube used as a high energy electrical switch. Triode, Tetrode and Pentode variations of the thyratron have been manufactured in the past, though most are of the triode design. Usable gases include mercury vapour, xenon, neon, and, in special high-voltage applications or applications requiring very short switching times, hydrogen, or deuterium.

An electric field is contemplated to be formed through the tube 18 with field components perpendicular to the parts 24 and 30. The beverage travelling in the tube 18 is then subjected to the electric field.

The grids 32 and 34 are coupled to a controllable electrical power source.

Generally, bacteria in the beverage are also subjected to this electric field. Bacteria have a lipid bilayer membrane. The lipid bilayer membrane is a membrane or zone of a membrane composed of lipid molecules, usually phospholipids. Lipids are amphiphilic molecules since they have polar head groups and non-polar fatty acid tails. The bilayer is composed of two layers of lipids arranged so that their hydrocarbon tails face one another to form an oily core held together by Van der Waals interactions, while their charged heads face the aqueous solutions on either side of the membrane. Electroporation, or electropermeabilization, of a cell is a significant increase in the electrical conductivity and permeability of the cell membrane caused by an externally applied electric field. This is also utilised in molecular biology. Pores are formed when the voltage across a plasma membrane exceeds its dielectric strength. If the strength of the applied electric field and/or duration of exposure to it are properly chosen, the pores formed by the electrical pulse reseal after a short period of time, during which extracellular compounds have a chance to enter into the cell. However, excessive exposure of live cells to electric fields may cause apoptosis and/or necrosis i.e. result in cell death.

The membrane shifts so that the membrane is turned inside out. The electric field is turned on and off causing the membrane to pulsate and eventually be destroyed.

The electric field may be pulsed with a frequency of e.g. 1000 Hz. The membrane is able to turn inside out in approximately 1 μsec-1 msec without being damaged. The system 10 still further comprises a wire 36.

The system 10 may be part of a brewery system, e.g. at the outlet of a boiler or e.g. just prior to a filling station where the beverage is filled in containers, e.g. bottles, cans or kegs.

The width of the beverage guiding tube 18 is in the order of 1 cm and the capacitor is charged to around $10^5$ V, resulting in the electric field having a field-strength in the order of $10^4$ V/mm.

FIG. 2a is a schematic view of one way of implementing the capacitor part of the system 10 in FIG. 1. Three plates 38, 40, and 42 form a capacitor-like structure. The plate 42 define a first counter-electrode 42a and a second counter electrode 42a connected to each other in a short-circuit connection. The first counter-electrode 42a provides, with a first electrode 47 defined by the plate 38, a first capacitor of a specific capacitance, and the second counter-electrode 42b provides, with a second electrode 48 defined by the plate 40, a second capacitor of a second specific capacitance. The first electrode 47 has a first part 47a adjacent a fluid conduit 50, and a second part 47b extending substantially perpendicular to the first part 47a. The second electrode 48 has a third part 48a adjacent the fluid conduit 50, and a fourth part 48b extending substantially perpendicular to the third part 48a. A dielectric medium 44 is used to maintain the distances between the plates 38 and 40 relative to the plate 42. The plates 38, 40, and 42 are made from an electrically conductive material. The coil 46 is an illustration of a conductive device connecting the two plates 38 and 40 for maintaining a substantially constant current. In alternative embodiments, other suitable electrical components may be used. The structure is repeatedly charged and discharged so as to cause an electric field to be generated between the first and second electrodes 47, 48 provided by the plates 38 and 40, respectively.

Between the first part 47a of the first electrode 47 and the first part 48a of the second electrode 48 the a beverage conduit or tube 50 is positioned. The conduit 50 is made from a non-conductive material, preferably plastic, glass, or the like. The beverage flows through the conduit 50 in a fluid path from a first end 51 to a second end 53 in the direction of the arrows 52 and 54.

The wires 56 and 58 are respectively connected to a first trigger point 60 on the second part 47b of the first electrode 47 and a second trigger point (not shown) on the first counter electrode 42a opposite the first trigger point 60. The wires 56, 58 are part of an electrical activation circuit used to short-circuit the system to generate an electric wave from the first trigger point 60. When the wires 56 and 58 are connected to their respective trigger points, as shown in FIG. 2a, and the circuit is activated, an electric wave travels toward the first part 47a of the first electrode 47. As described above, the beverage in the conduit 50 is subjected to the electric field, and the electric field is pulsed with a frequency around 1000 Hz. This causes the polar double membrane of the bacteria to flip-flop inside-out and eventually destroys the membrane, thereby killing the bacteria. The electric field is changed at such a high speed that the bacteria are not able to adapt, and they undergo many periods during the travel of the beverage from the inlet of the conduit 50 to the outlet.

Figure 2B:
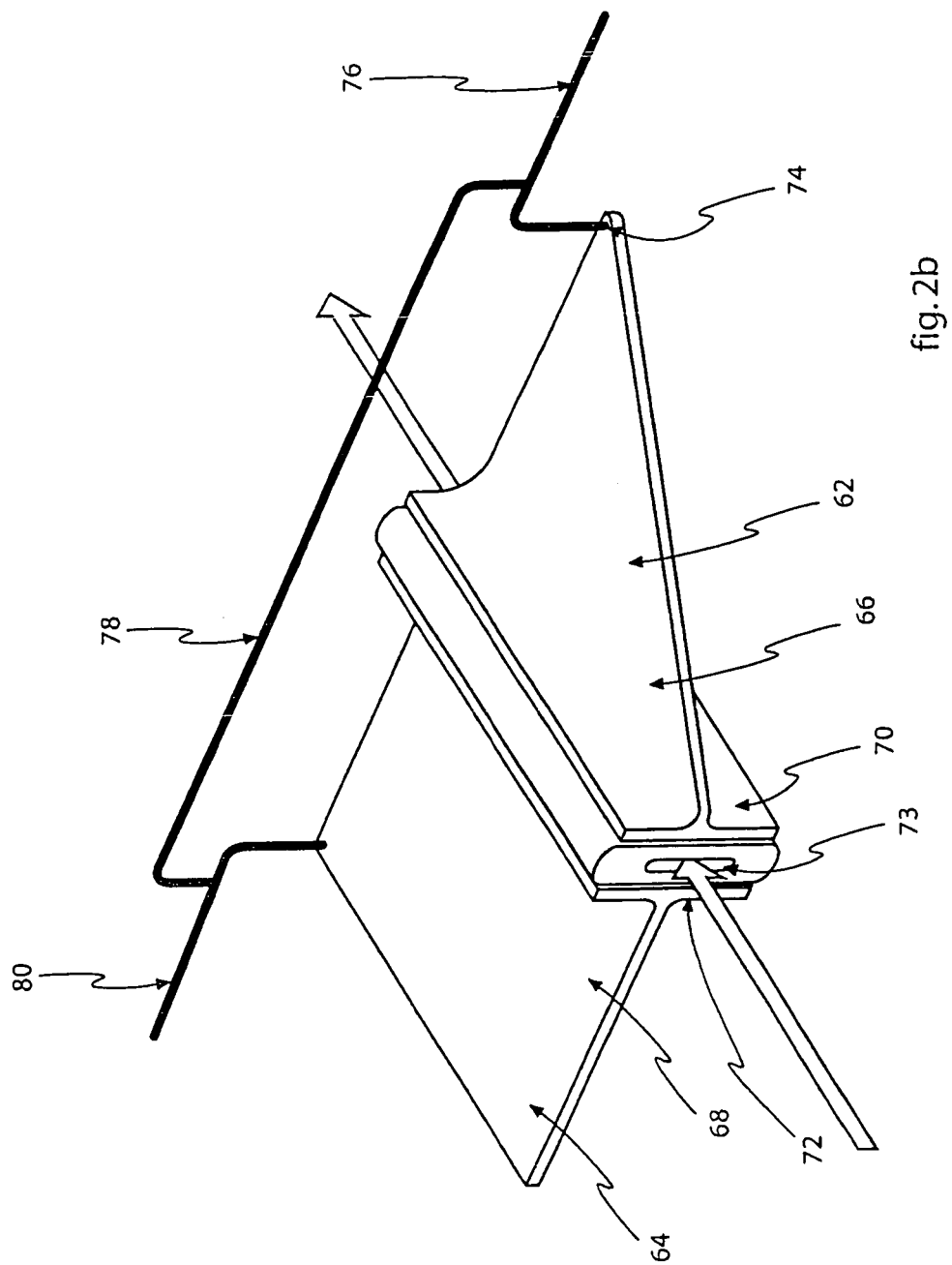

FIG. 2b is a schematic view of another way of implementing the capacitor part of the system 10 in FIG. 1

The capacitor part comprises two plates 62 and 64. Each plate 62, 64 comprises a first part 66 and 68, respectively, and a second part 70, 72 positioned perpendicular to the first part 66 and 68, respectively. Beverage flows in the channel 73, which is positioned in between the parts 70 and 72.

As an electric field emanates from the point at 74 from the coaxial cable 76, the first part 66 of the plate 62 may be triangular shaped, thus reducing material and space use.

An electrical connection 78 between two coaxial cables 76 and 80 is established. The connection 78 is between the screen of the coaxial cables 76 and 80 and not the core parts.

FIGS. 3 to 8 are schematic illustrations of a sterilisation device embedded or included in a beverage guiding tube or pipe. The sterilisation device utilises the metal in the tube or pipe to generate the electric field.

Figure 3:
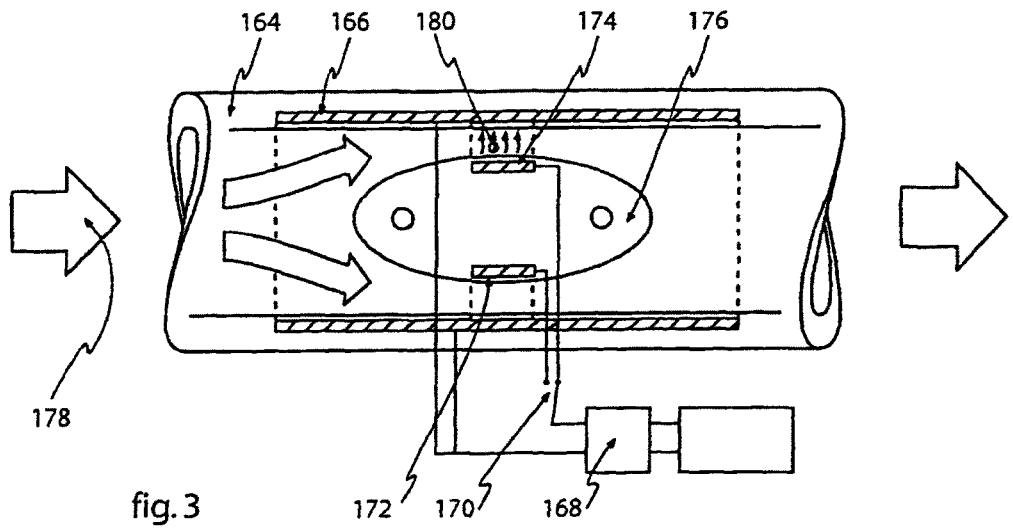
FIGS. 3 to 8 are schematic illustrations of tubes with integrated sterilisation devices.

FIG. 3 schematically illustrates a section of a pipe or tube 164. An encircling electrode 166 is embedded in the tube 164. Electrical connections from a power source 168 are provided. A switch 170 allows switching between two electrodes 172 and 174 on a body 176 inside the tube 164. This allows an electric field, indicated by the arrows 180, to be generated between the electrode 174 and the electrode 166.

Figure 4:
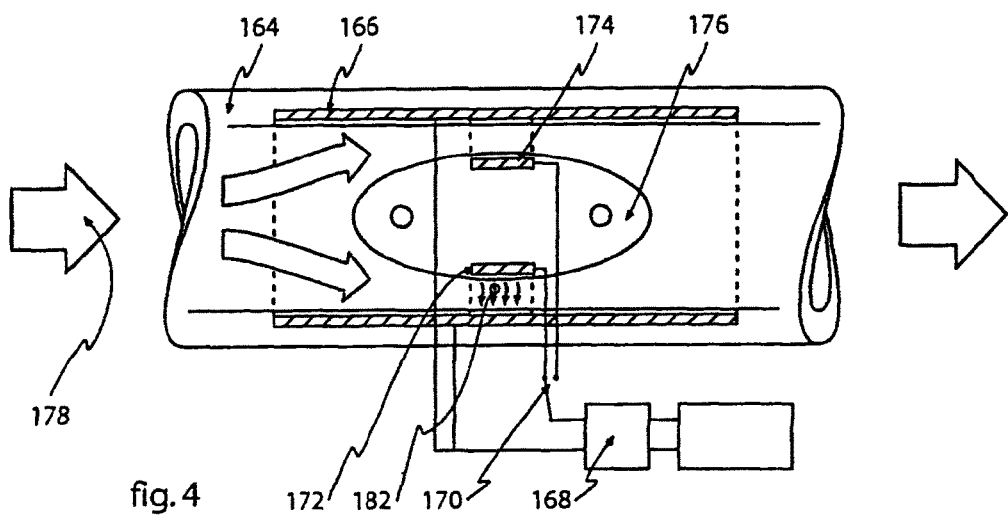

FIG. 4 schematically illustrates the same section of pipe 164 shown in FIG. 3. In FIG. 4 however, an electric field, as indicated by the arrows 182, is generated between the electrode 172 and the electrode 166.

The body 176 causes beverage to flow in the direction of the arrow 178. Numerals identical to those in FIG. 3 denote similar elements.

Figure 5:
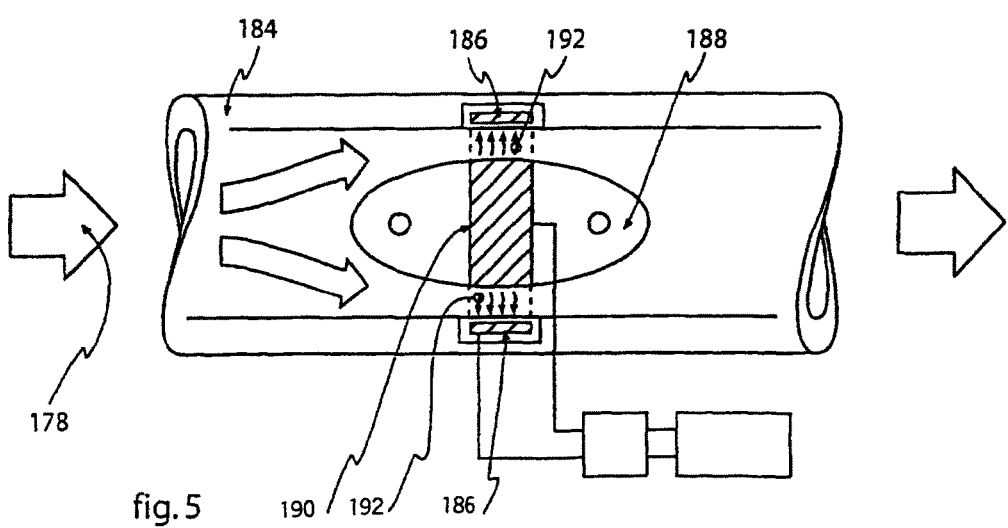

FIG. 5 schematically illustrates a section of a pipe 184 with an electrode 186 embedded therein. A body 188 is positioned within the tube 184. The body 188 includes an electrode 190. An electric field 192 is generated between the electrode 186 and the electrode 190. The arrow 178 indicates the flow of beverage.

Figure 6:
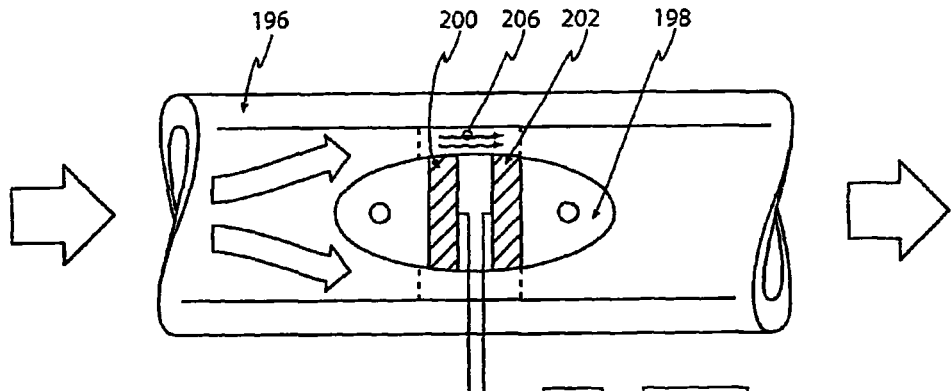

FIG. 6 schematically illustrates a section of a pipe 196 with a body 198. The body includes two electrodes 200 and 202.

Electrical power is supplied from the power supply 204. The electrical currents in the electrodes generate an electric field 206 in the beverage.

Figure 7:
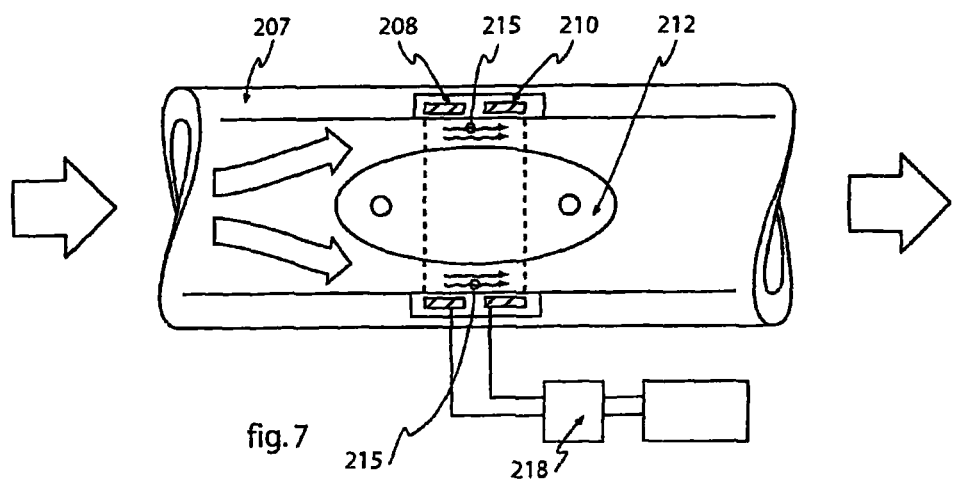

FIG. 7 schematically illustrates a section of a pipe 207 where two electrodes 208 and 210 are embedded in the pipe 207. Beverage flows around a body 212 inside the pipe 207. Electrical power is supplied from the power supply 218. Electric field is indicated by arrows 215.

Figure 8:
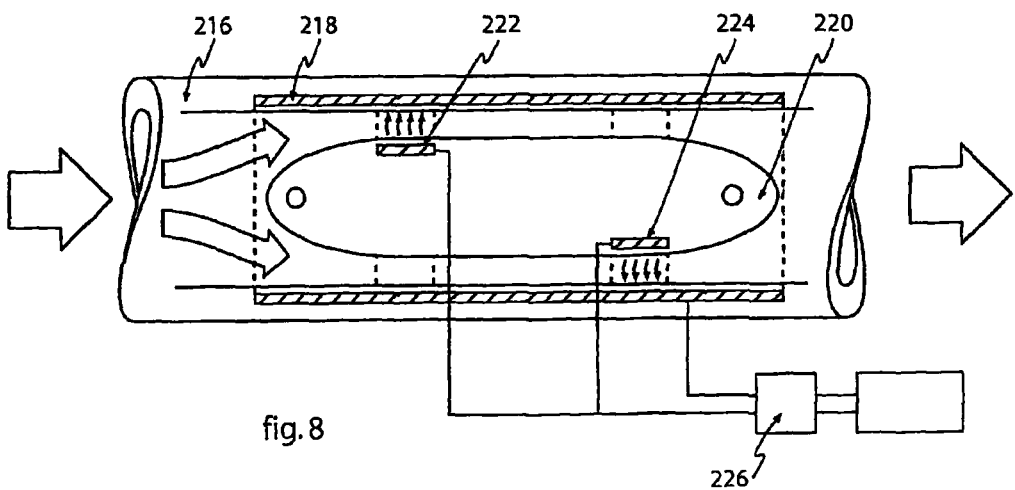

FIG. 8 schematically illustrates a pipe 216 with an electrode 218 embedded therein. A body 220 is positioned within the pipe 216. Two electrodes 222 and 224 are embedded in the body 220. The two electrodes 222 and 224 are supplied with electrical power from power supply 226.

In the embodiments in the above figures where two electrodes are shown, the two electrodes may be activated simultaneously or independently or alternating or combinations thereof.

Figure 9A:
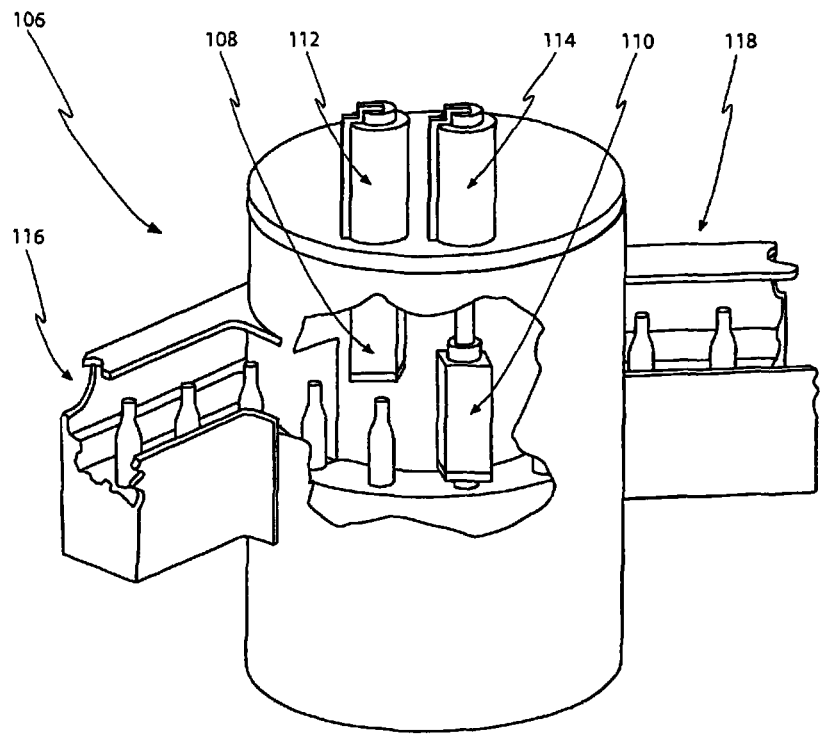
FIG. 9a is a schematic illustration of an apparatus incorporating a sterilisation device for sterilising beverage in containers.

FIG. 9a is a schematic illustration of a system 106 for sterilisation of beverage in containers, specifically for sterilisation of beverage in glass containers, i.e. glass bottles. The system 106 includes two electric field generators 108 and 110. The generators are movable in one direction so that they may surround a bottle. When the bottle is surrounded by the field generator, an electric field is applied which field then penetrates the bottle and interacts with the double lipid membrane as described elsewhere in the present specification.

The two electric field generators 108 and 110 are reciprocally moved by the apparatuses 112 and 114. The two electric field generators 108 and 110 are moved in a direction substantially parallel to the longitudinal axis of the containers, i.e. the bottles shown.

The bottles are supplied or transported via a conveyor system 116 and after sterilisation the bottles are transported further by a second conveyor system 118. The bottles are supplied to the sterilisation system after being filled with a beverage and being fitted with a cap. In alternative embodiments the cap may be applied later. The bottles are transported to further treatment or packaging stations.

In a further alternative embodiment the system 106 may be used to sterilise empty bottles.

Figure 9B:
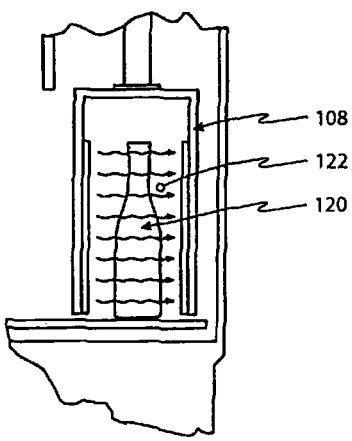
FIG. 9b is a zoomed view of the apparatus of FIG. 9a, FIG. 9c is a schematic illustration of an apparatus for filling containers with a beverage and incorporating a sterilisation device for sterilising beverage as it is being dispensed.

FIG. 9b is a schematic cut-through view of a bottle 120 inside the electric field generator 108. The electric field is indicated by the wavy lines 122. The electric field is not affected to any substantial effect by the metallic cap.

Figure 9C:
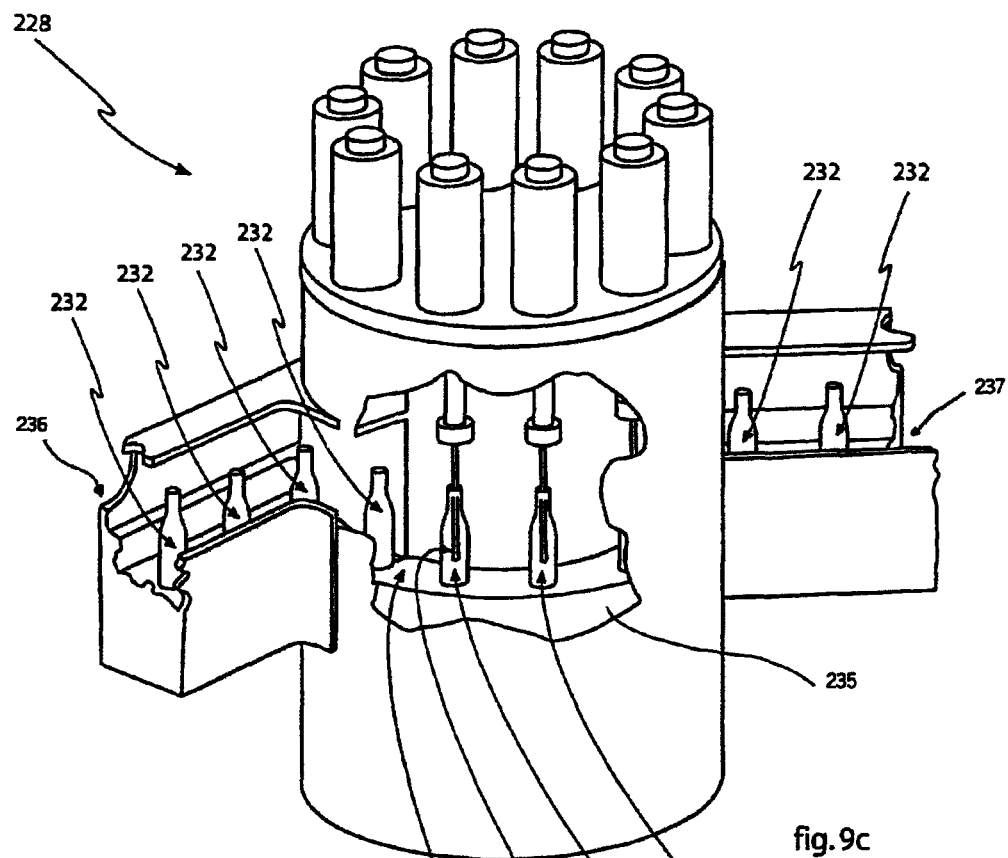
FIG. 9d is a zoomed view of the apparatus of FIG. 9c.

FIG. 9c is a schematic illustration of a system 228 for sterilisation of beverage in containers, specifically for sterilisation of beverage in glass containers, i.e. glass bottles. The main difference compared to the system 106 illustrated above is that the system 228 sterilises the beverage as it is being transferred into a specific container. It is assumed that the container itself has been cleaned and sterilised.

The system 228 comprises a plurality of beverage dispensing rods or guides 230 which are rotated counter clock-wise, i.e. in the same direction as the containers 232 on the conveyor system 234. Each of the containers 232, e.g. glass bottles, is filled during the travel from the inlet at 236 to the opposite outlet at 237. The rods 230 are movable in a direction parallel to the longitudinal axis of the containers, i.e. up and down.

Figure 9D:
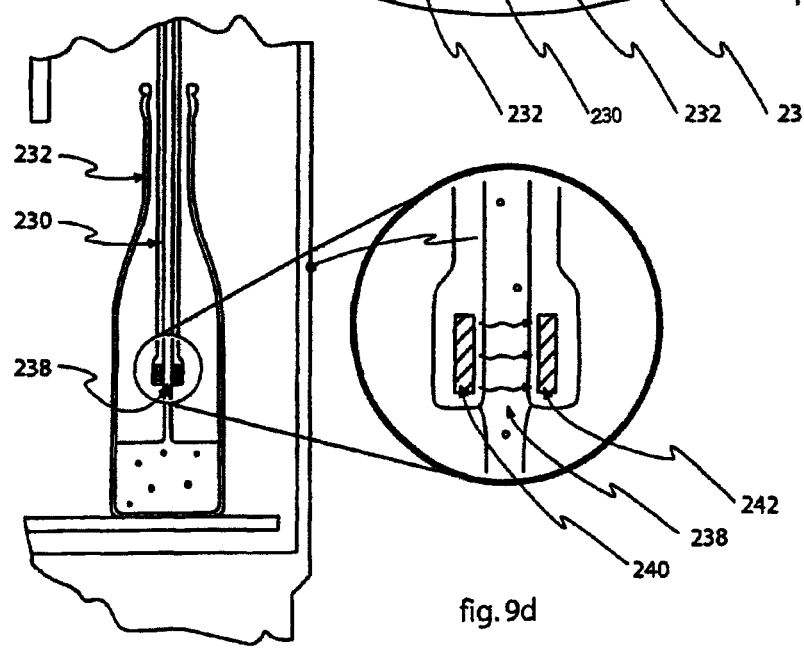

FIG. 9d is a schematic zoomed view of a container 232 being filled via a rod 230. At the open end 238 of the rod 230 two electrodes 240 and 242 are positioned. The electrodes 240 and 242 are part of a beverage sterilisation device according to the present invention, and as described throughout the present description.

Advantageously, a flow meter may be incorporated in the rod or in the system 228, so that the electrodes 240 and 242 only produce an electric field when beverage is being filled into a container. Alternatively an electric field may also be produced when no beverage is being dispensed so that it is ensured that no contaminants are present in the rod 230 before passing beverage into a container.

FIG. 10 is a schematic illustration of an alternative way of sterilising a beverage in a container 124. In general, the container may be metallic or conductive or at least partly conductive and may include coating or be at least partly coated. The container may further be a can, keg or bottle. An electrode 126 is lowered into the beverage 128. An electric field is generated in the beverage 128 between the electrode 126 and the can 124. The can 124 comprises a coating on the inner wall so that the electric field does not cause any material of the wall of the can 124 to be dissolved in the beverage due to electrolytic processes caused by the presence of the electric field or any other form of chemical interaction between the wall and the beverage.

FIGS. 11a and 11b schematically illustrate the setup and circuit diagram, respectively. FIG. 11a shows two plates 82 and 84 between which a beverage guide 86 is located. A coil 88 connects the two plates 82 and 84. The two plates 82 and 84 share a common plate 90 establishing the capacitor system described above.

FIG. 11b schematically shows a circuit including two capacitors 92 and 94 having a common electrode 96. A voltage of $U_{Bo}$ is applied at 98 while 100 is kept at 0 V. The coil 102 ensures that a voltage is maintained over the two capacitors 92 and 94. The circuit further comprises a spark gap 104.

FIGS. 12a and 12b are schematic views of a system 146 for sterilising beverage in a production facility. The system 146 receives a flow of beverage via inlet 148. The beverage flows with a laminar flow. The inlet section 148 has a circular cross-sectional geometry. The beverage travels in the direction indicated by the arrow 150.

The beverage flows from the inlet 148 to a first transitional section 152. The geometry at the inlet of the first transitional section 152 corresponds to the geometry of the inlet section 148. The first transitional section 152 changes shape in that it becomes thinner and wider, from a substantially circular cross-section to a more rectangular cross-section. The change in the cross-section is formed gradually so that the flow of the beverage is kept a substantially laminar flow. As described above, a small amount of non-laminar flow may be acceptable.

The first transitional section 152 is joined to a second transitional section 154 which provides an opposite transition from a substantially rectangular cross-section to a substantially circular cross-section. The second transitional section 154 is connected to an outlet section 162. At the interface 156 between the first 152 and the second 154 transitional sections, an electrode 158 is positioned. On the opposite side of the interface 156, a second electrode 160 is positioned parallel to the first electrode 158. The two electrodes together allow an electric field to be transmitted through the beverage in the system 146.

The electric field generated by the electrodes 158 and 160 may be stationary or pulsed, either periodically with a fixed frequency such as 1 kHz, or within a frequency band or interval.

The system 146 is preferably made from a non-electrical conductive material, preferably either glass or PTFE (e.g., Teflon®). Alternatively any other suitable material may be used.

FIGS. 13a and 13b are schematic illustrations of a sterilisation device 130 attached to a beverage dispensing line 132. The beverage dispensing line 132 may be part of a bar setting or the like. Also, the sterilisation device 130 may be included in a water dispensing apparatus. The sterilisation device 130 is formed by two halves 134 and 136 where a recess is formed in each half, so that when assembling the two halves, a tube may be received in the opening or passage formed by the recesses.

The tube or dispensing line 132 may be made from glass or PTFE (e.g. Teflon®) or any other suitable material.

The embodiment shown in FIGS. 13a and 13b has an electrode 138 and 140 in each half, as indicated by the punctured or dashed lines. In alternative embodiments the electrodes may be placed in one half only. The halves need not be identical, e.g. an embodiment with one part being significantly larger than the other may be implemented, e.g. a tube receiving part and a corresponding lid or other tube retaining means.

FIGS. 14a and 14b schematically illustrate a further embodiment of a sterilisation device 142. A tube 144 passes through a passage in the housing of the device 142. In alternative embodiments, the device 142 may include fastening means or couplings for coupling the device 142 to a tube, so that beverage flows through the device 142, in a manner similar to the device shown in FIG. 1.

The embodiment in FIGS. 13a and 13b as well as the embodiment in FIGS. 14a and 14b include an electrical power source inside the housing, power source not illustrated. The power source is a battery. As the effect used by the device is low, a standard battery may provide a sufficiently long service life. A battery level indicator may be included for allowing inspection of the status of the power source.

FIG. 15a is a schematic view of a system 244 comprising three beverage storage containers 246, 248 and 250. The containers 246, 248 and 250 are via pipes 252, 254 and 256 connected to a tap 258. Pressure medium is supplied to the containers 246, 248 and 250 from a pressure medium storage 260. In this embodiment the pressure medium is $CO_2$.

Each of the containers 246, 248 and 250 is connected to the pipes 252, 254, 256 via a coupling device 262 as shown in FIG. 15c. The device 262 comprises a handle 264 operable between an open state, where beverage is allowed to exit a respective container, and a closed state where beverage does not enter a respective pipe or tube. In the closed state it is also possible to exchange a container, e.g. when it has been emptied.

The tube 266 shown in FIG. 15c comprises a beverage sterilisation device according to the teachings of the present invention. The beverage sterilisation device ensures that no contamination in the form of bacteria and other micro organisms are allowed to enter a pipe or tube alive. It is contemplated that there may be a risk of contamination when exchanging or changing a beverage container. This leaves the coupling device 262 exposed to the surrounding environment and thus also to exposure of bacteria and other micro organisms as described above. The presence of a beverage sterilisation device at the coupling between a beverage container and the pipe or tube system is contemplated to provide a cleaner beverage compared to systems not including such a device.

At the tapping device 258, as shown in the zoomed schematic view in FIG. 15b, a beverage sterilisation device according to the basic teachings of the present invention is present, represented by the electrodes 268 and 270. Similar to the case at the coupling device 262 the tap 258 is exposed to the surrounding environment, but the beverage dispensing tip 272 is continuously exposed, possibly allowing micro organisms such as bacteria to enter the tip 272.

A flow meter as discussed above may be included in the tap 258 to allow distinction between situations where beverage is being dispensed and situations where no beverage is being dispensed. Alternatively a sensor may detect the position of the handle 274. The tap 258 is usually placed in a bar or the like.

In situations where no beverage is dispensed via the tap 258 the beverage sterilisation device may transmit or generate the electric field to kill micro organisms at a first rate, e.g. with a frequency of 1 Hz. When beverage is being dispensed, the beverage sterilisation device may transmit or generate the electric field to kill micro organisms at a second rate, e.g. with a frequency of 1000 Hz.

Figure 16:
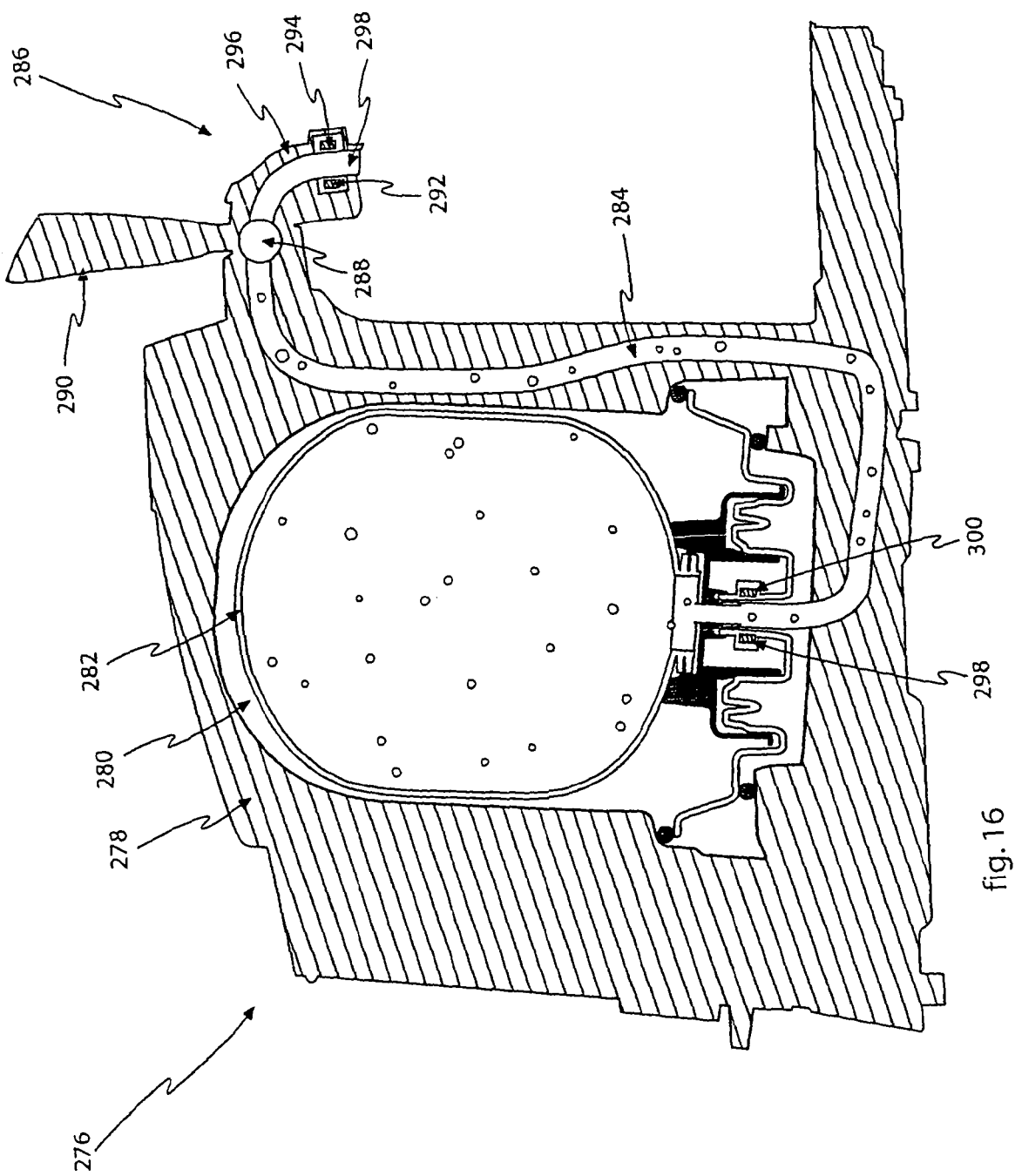
FIG. 16 is a schematic illustration of a draught beer dispensing system.

FIG. 16 is a schematic view of a system 276 for dispensing draught beer. The system 276 comprises a housing 278 with a pressure chamber 280 wherein a beverage container 282 is received. The system illustrated uses a flexible, collapsible beverage container 282, which is compressed by a gas, preferably $CO_2$ is used, but other gases may be usable. The beverage container 282 is in fluid communication with a beverage tube 284. The tube 284 is further in fluid communication with a tap 286. A valve 288 is controlled by the handle 290 for selectively dispensing beverage, i.e. draught beer.

A sterilisation device, illustrated by the two blocks 292 and 294, is mounted in the tip 296 of the tap. In the tip 296 an open-ended channel 298 is formed for dispensing beverage. After beverage has been dispensed though the channel 298 a small liquid film is bound to be formed at the walls of the channel 298, also there is a possibility that liquid drops are formed in the inner wall. As the open-ended channel 298 is exposed to the surrounding environment there is a risk that micro organisms, such as bacteria and the like, e.g. airborne or present on the outer surface of the tip, enter the open-ended channel 298.

In order to ensure that the beverage dispensed is not contaminated, the sterilisation device 292 and 294 may be operated both when beverage is being dispensed, and when no beverage is being dispensed. When beverage is being dispensed the beverage sterilisation device may be operated at a high frequency, e.g. 1000 Hz, meaning that an electric field is generated 1000 times each second.

When beverage is not being dispensed then it is possible to reduce the frequency and thereby reduce energy consumption.

If a water or beverage film is formed on the inside of the channel 298, and no beverage is flowing through the channel, any micro organisms present therein will travel or move relatively slowly. Therefore it is not necessary to use the sterilisation device as frequent to ensure that the channel is kept clean, or at least to keep bacteria from being present in the channel 298.

In the embodiment shown in FIG. 16 the elements 292 and 294 are relatively small compared to the tip 296, but in other embodiments these elements may have a larger extent, e.g. along the entire length of the channel 198 from the open end to valve 288.

In the housing 278 at the point where the tube 284 is connected to the beverage container 282 a second beverage sterilisation device, indicated by the elements 298 and 300, is positioned. The second sterilisation device is contemplated to ensure that micro organisms do not enter the tube 284 from the area around the connection between the tube 284 and the beverage container 282.

The beverage container 282 is replaceable and when replacing an empty beverage container with a filled one, there is a risk that the tube and/or connection may be exposed to micro organisms.

As the area at the second beverage sterilisation device is not exposed to surroundings the second beverage sterilisation device does not need to be operated at the same frequency as the first beverage sterilisation device at the tip. The second beverage sterilisation device may also be connected or controlled by the detection of flow of beverage, e.g. flow sensor or the state of the handle 290, e.g. as described in relation to the embodiment shown in FIGS. 15a, b and c.

It is contemplated that the presence of two beverage sterilisation devices, one at each end of the tube 284, ensures that the beverage present in the tube 284 between the valve 288 and the beverage container is not contaminated, and therefore does not contaminate the beverage present in the beverage container 282.

The invention claimed is:

1. A method of sterilizing a beverage, said method comprising the steps of:
   (a) providing a sterilization device, comprising:
      a conduit defining an electrically insulated fluid path;
      a first electrically conductive electrode having a first part and a second part, said first part being positioned adjacent to said fluid path at said conduit, said second part extending in a plane substantially perpendicular to said first part;
      a conductive plate defining first and second electrically conductive counter electrodes connected to each other in a short-circuit electrical connection, the first electrically conductive counter electrode defining, with said first electrically conductive electrode, a first capacitor of a first specific capacitance;
      a second electrically conductive electrode having a third part and a fourth part, said third part being positioned adjacent to said fluid path at said conduit, said fourth part extending in a plane substantially perpendicular to said third part and away from said second part of said first electrically conductive electrode;
      the second electrically conductive counter electrode defining, with said second electrically conductive electrode, a second capacitor of a second specific capacitance;
      a conductive device electrically connected between said first electrically conductive electrode and said second electrically conductive electrode;
      a first trigger point being defined at said second part of said first electrically conductive electrode and remote from said first part thereof, and a second trigger point being defined at the first electrically conductive counter electrode opposite to said first trigger point; and
      an electrical activation circuit connected to said first and second trigger points and operable for short-circuiting said first and second trigger points and for causing an electric field to propagate from said first trigger point and along said fluid path;
   (b) conducting said beverage through said electrically insulated fluid path;
   (c) charging said first and said second electrically conductive electrodes;
   (d) activating said electrical activation circuit so as to generate an electric field along said electrically insulated fluid path; and
   (e) repeating said charging step and said activating step.

2. The method according to claim 1, wherein said charging step and said activating step are repeated with a frequency of 10 Hz to 1000 Hz for a first period of time.

3. The method according to claim 2, wherein said charging step and said activating step are repeated non-periodically for a second period of time.

4. The method according to claim 3, wherein said second period of time is 1 μsec-1 msec.

5. A method of sterilising a beverage conducted in an electrically insulated fluid path, said method comprising:
   (a) providing a sterilisation device comprising:
      (i) a housing defining an outer surface and an inner space, said housing having a first end and a second end, said electrically insulated fluid path defining a conduit formed by said outer surface and adapted to receive a tube, said conduit having an open part for receiving said tube;
      (ii) a first electrically conductive electrode having a first part and a second part, said first part being positioned adjacent to said fluid path at said conduit, said second part extending substantially perpendicular to said first part;
      (iii) a conductive plate defining first and second electrically conductive counter electrodes connected to each other in a short-circuit electrical connection first electrically conductive counter electrode defining, together with said first electrical conductive electrode, a first capacitor of a first specific capacitance;
      (iv) the second electrically conductive electrode having a third part and a fourth part, said third part being positioned adjacent to said fluid path at said conduit, said fourth part extending substantially perpendicular to said third part and away from said second part of said first electrically conductive electrode;
      (v) a second electrically conductive counter electrode defining, together with said second electrically conductive electrode, a second capacitor of a second specific capacitance, wherein said first electrically conductive counter electrode and said second electrically conductive counter electrode are short-circuited by an electrical connection;
      (vi) a constant current maintaining inductor electrically connected between said first electrically conductive electrode and said second electrically conductive electrode;
      (vii) a first trigger point being defined at said second part of said first electrically conductive electrode and remote from said first part thereof, and a second trigger point being defined at the first electrically conductive counter electrode opposite to said first trigger point; and
      (viii) an electrical activation circuit for short-circuiting said pair of trigger points and for causing an electric field to propagate from said first trigger point and along said fluid path;
   (b) providing said beverage in said electrically insulated fluid path;
   (c) charging said first and said second electrically conductive electrodes;
   (d) activating said activation circuit so as to generate an electric field through said electrically insulated fluid path; and
   (e) repeating said charging step and said activating step.

6. The method according to claim 5, wherein said charging step and said activating step are repeated with a frequency of 10 Hz to 1000 Hz for a first period of time.

7. The method according to claim 6, wherein said charging step and said activating step are repeated non-periodically for a second period of time.

8. The method according to claim 7, wherein said second period of time is 1 μsec -1 msec.

\* \* \* \* \*

UNITED STATES PATENT AND TRADEMARK OFFICE
CERTIFICATE OF CORRECTION

PATENT NO. : 8,894,833 B2
APPLICATION NO. : 12/739705
DATED : November 25, 2014
INVENTOR(S) : Jan Norager Rasmussen et al.

It is certified that error appears in the above-identified patent and that said Letters Patent is hereby corrected as shown below:

In the Specification:

In column 8, line 57, delete "beverage however;" and insert -- beverage; however, --, therefor.

In column 8, line 64, delete "RE-" and insert -- RF- --, therefor.

In column 11, line 48, delete "define" and insert -- defines --, therefor.

In column 11, line 50, delete "42a" and insert -- 42b --, therefor.

In column 11, line 52, before "specific" insert -- first --.

In column 11, line 53, delete "42bprovides," and insert -- 42b provides, --, therefor.

In column 12, line 5, after "the" delete "a".

In the Claims:

In column 18, line 26, in claim 5, after "connection" insert -- the --.

Signed and Sealed this
Fifth Day of May, 2015

Michelle K. Lee
*Director of the United States Patent and Trademark Office*